(12) United States Patent
Matsumoto et al.

(10) Patent No.: US 11,534,621 B2
(45) Date of Patent: Dec. 27, 2022

(54) LIGHT TREATMENT SYSTEM AND LIGHT TREATMENT METHOD

(71) Applicant: OLYMPUS CORPORATION, Tokyo (JP)

(72) Inventors: Koji Matsumoto, Tokyo (JP); Mitsuru Namiki, Hanno (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/186,360

(22) Filed: Feb. 26, 2021

(65) Prior Publication Data

US 2021/0178176 A1    Jun. 17, 2021

Related U.S. Application Data

(63) Continuation of application No. PCT/JP2018/040597, filed on Oct. 31, 2018.

(51) Int. Cl.
*A61N 5/06*    (2006.01)

(52) U.S. Cl.
CPC .......... *A61N 5/0603* (2013.01); *A61N 5/062* (2013.01); *A61N 2005/061* (2013.01); *A61N 2005/063* (2013.01)

(58) Field of Classification Search
CPC ...... A61N 5/0603; A61N 5/062; A61N 5/067; A61N 2005/061; A61N 2005/0626; A61N 2005/063; A61N 2005/0664
See application file for complete search history.

(56) References Cited

U.S. PATENT DOCUMENTS

| 4,612,938 A | 9/1986 | Dietrich et al. |
| 4,612,939 A | 9/1986 | Dietrich et al. |
| 6,096,030 A * | 8/2000 | Ortiz .................... A61N 5/0601 606/14 |

(Continued)

FOREIGN PATENT DOCUMENTS

| JP | 59-95065 A | 5/1984 |
| JP | 2005-531336 A | 10/2005 |

(Continued)

OTHER PUBLICATIONS

Kim H, Chang JH. Increased light penetration due to ultrasound-induced air bubbles in optical scattering media. Sci Rep. Nov. 23, 2017;7(1):16105. doi: 10.1038/s41598-017-16444-9. PMID: 29170545; PMCID: PMC5701037. (Year: 2017).*

(Continued)

*Primary Examiner* — Mallika D Fairchild
*Assistant Examiner* — Shreya Anjaria
(74) *Attorney, Agent, or Firm* — Scully, Scott, Murphy & Presser, P.C.

(57) ABSTRACT

A light treatment system includes: a probe configured to be inserted into a body cavity, the probe including an optical fiber configured to propagate light, and a light emitter that is provided at a distal end of the optical fiber, the emitter being configured to emit the light; a balloon catheter into which the probe is inserted, the balloon catheter including a distal end portion that is to be inserted into the body cavity and that is to be dilated by being supplied with a liquid including air bubbles; and an air bubble generator configured to generate the air bubbles to be included in the liquid and change a property of the air bubbles.

15 Claims, 7 Drawing Sheets

(56) References Cited

U.S. PATENT DOCUMENTS

2004/0039242 A1    2/2004  Tolkoff et al.
2017/0265942 A1*   9/2017  Grace .................. A61B 18/245
2018/0193613 A1*   7/2018  Melsky ................. A61B 18/00

FOREIGN PATENT DOCUMENTS

JP      2013-220126 A        10/2013
WO         03/084601 A2      10/2003
WO    WO-2016109736 A1 *     7/2016   ....... A61B 17/22004

OTHER PUBLICATIONS

International Search Report dated Jan. 29, 2019 received in PCT/JP2018/040597.

* cited by examiner

FIG.4

| | Type1 | Type2 | Type3 | Type4 | Type5 |
|---|---|---|---|---|---|
| LARGEST DIAMETER OF BALLOON [cm] | 7 | 7 | 7 | 7 | 7 |
| NA OF LIGHT SOURCE | 0.5 | 0.5 | 0.5 | 0.5 | 0.5 |
| POSITION OF LIGHT SOURCE | MIDDLE | MIDDLE | MIDDLE | MIDDLE | MIDDLE |
| DIAMETER OF LIGHT EMITTER [$\mu m$] | 200 | 200 | 200 | 200 | 200 |
| REFRACTIVE INDEX OF AQUEOUS SOLUTION | 1.3 | 1.3 | 1.3 | 1.3 | 1.3 |
| DIAMETER OF AIR BUBBLES [$\mu m$] | 10 | 10 | 10 | 5 | 3 |
| NUMBER OF AIR BUBBLES [/cm$^3$] | 3000 | 6000 | 12000 | 12000 | 12000 |

LIGHT TREATMENT SYSTEM AND LIGHT TREATMENT METHOD

CROSS-REFERENCE TO RELATED APPLICATION

This application is a continuation of International Application No. PCT/JP2018/040597, filed on Oct. 31, 2018, the entire contents of which are incorporated herein by reference.

BACKGROUND

1. Technical Field

The present disclosure relates to light treatment systems and light treatment methods.

2. Related Art

Light treatment systems for performing treatment using light have been known (see, for example, Japanese Patent Application Laid-open No. S59-095065). In these light treatment systems, a sac-like balloon is attached to a distal end of a tubular catheter to be inserted into the body cavity of a human body, such as the bladder. A light conductor, such as optical fiber, is inserted in the catheter and a light emitter at a distal end of the light conductor is placed in the balloon. The light emitter emits treatment light forward. Such treatment is called photodynamic therapy (PDT).

In this technique, the balloon is filled with a scattering medium including fat emulsion diluted with a physiological saline solution. The treatment light is thereby scattered and not only the upper part of the bladder, but also the lower part of the bladder is able to be irradiated with the treatment light.

The upper part of the bladder is able to be observed using a rigid endoscope inserted from the urethra. A tumor in the upper part of the bladder is able to be removed by a looped electrosurgical knife, for example. This treatment is called a transurethral resection of a bladder tumor or a TUR-Bt. The lower part of the bladder on the other hand has a prostate therearound and is a part where a tumor tends to be generated. However, because the lower part of the bladder is positioned behind the rigid endoscope that has been inserted in the bladder, a tumor therein is difficult to be detected and the lower part of the bladder is also a part where some of a tumor tends to remain after excision. Therefore, treatment additionally using a light treatment system is desired for lower parts of bladders.

SUMMARY

In some embodiments, a light treatment system includes: a probe configured to be inserted into a body cavity, the probe including an optical fiber configured to propagate light, and a light emitter that is provided at a distal end of the optical fiber, the emitter being configured to emit the light; a balloon catheter into which the probe is inserted, the balloon catheter including a distal end portion that is to be inserted into the body cavity and that is to be dilated by being supplied with a liquid including air bubbles; and an air bubble generator configured to generate the air bubbles to be included in the liquid and change a property of the air bubbles.

In some embodiments, a light treatment method includes: inserting a balloon catheter and a probe into a body cavity, the balloon catheter including a distal end portion that is dilatable, the probe being configured to propagate light for treatment and emit the light propagated, the probe being configured to be inserted into the balloon catheter; fixing the distal end portion in the body cavity by circulating a liquid through the distal end portion to dilate the distal end portion; starting a process of generating air bubbles and causing the air bubbles to be included in the liquid; and irradiating inside of the body cavity with the light from the probe.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 4 is a diagram illustrating an example of settings of parameters for treatment;

DETAILED DESCRIPTION

Modes for implementing the disclosure (hereinafter, referred to as "embodiments") will be described below by reference to the appended drawings.

Figure 1:
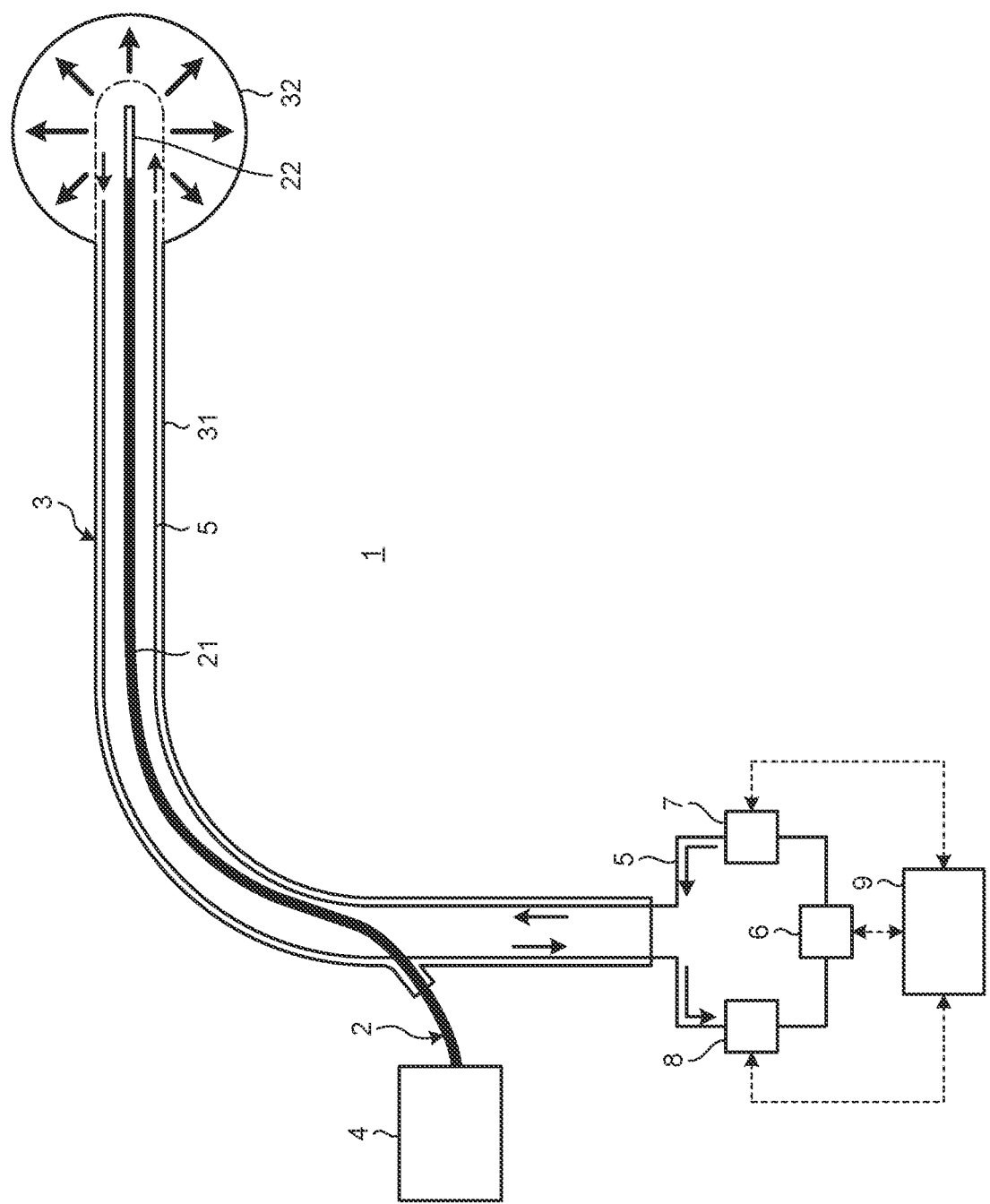
FIG. 1 is a diagram illustrating a configuration of main parts of a light treatment system according to an embodiment.

FIG. 1 is a diagram illustrating a configuration of main parts of a light treatment system according to an embodiment. A light treatment system 1 illustrated in FIG. 1 is a system for treating a bladder by using light.

The light treatment system 1 includes a probe 2, a balloon catheter 3, a light source device 4, a pipe line 5, an air bubble generator 6, a circulation generator 7, an air bubble detecting device 8, and a control device 9.

The probe 2 includes: an optical fiber 21 that is made of glass or plastic and propagates light for treatment; and a light emitter 22 that is provided at a distal end of the optical fiber 21 and emits light propagated through the optical fiber 21. The light emitter 22 is cylindrical and has a diffusing function of emitting light in all directions by scattering the light. The probe 2 is flexible and is able to be inserted into the bladder via the urethra of a human body.

The balloon catheter 3 includes: a main body 31 through which the probe 2 is able to be inserted; and a distal end portion 32 that is provided at a distal end of the main body 31 and is spherically dilatable in a bladder. By the distal end portion 32 reaching a bladder and being dilated therein, position of the distal end portion 32 in the bladder is fixed.

The light emitter 22 of the probe 2 reaches the inside of the distal end portion 32, and by the distal end portion 32 being fixed in the bladder, position of the probe 2 in the bladder is fixed. Furthermore, a flow outlet and a flow inlet of the pipe line 5 reach the inside of the distal end portion 32 and when the balloon catheter 3 is being used, the distal end portion 32 is filled with a liquid including air bubbles. This liquid is, for example, a physiological saline solution. By controlling flow rate and/or pressure of this liquid, the light treatment system 1 dilates the distal end portion 32 to a freely-selected size to define size of the bladder and fix the position of the balloon catheter 3 relatively to the bladder.

The balloon catheter 3 is made of a material that is thin, elastic, and transparent. This material may be, for example, natural rubber, silicone rubber, or thermoplastic elastomer.

The light source device 4 generates light for treatment to be supplied to an end surface of the optical fiber 21, the end surface being at a proximal end of the optical fiber 21. The light generated by the light source device 4 is, for example, laser light.

The pipe line 5 is a flow channel for the liquid including air bubbles. The pipe line 5 passes through the balloon catheter 3 and includes the flow outlet and the flow inlet both inside the distal end portion 32. The flow inlet is provided to collect the liquid including air bubbles that have passed through the balloon catheter 3 and changed in size. Furthermore, the air bubble generator 6, the circulation generator 7, and the air bubble detecting device 8, which will be described later, are provided at positions on the pipe line 5.

Figure 2:
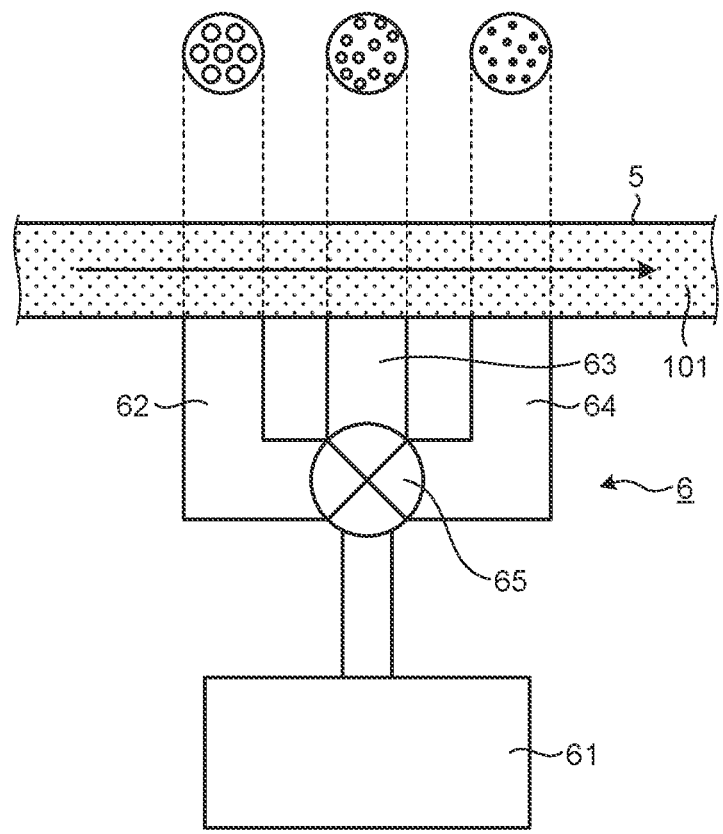
FIG. 2 is a schematic enlarged view of a configuration of an air bubble generator.

The air bubble generator 6 causes the liquid flowing through the pipe line 5 to include air bubbles. FIG. 2 is a schematic enlarged view of a configuration of the air bubble generator 6. In FIG. 2, a rightward arrow written in the pipe line 5 indicates the direction in which a liquid 101 flows. The air bubble generator 6 includes an air generator 61, three air feeding pipes 62 to 64, and a switching unit 65. The air bubble generator 6 is able to not send air bubbles to the pipe line 5, by keeping air at a certain pressure.

The air generator 61 is able to change pressure of air generated, under control of the control device 9. The number of air bubbles generated by the air bubble generator 6 is thereby able to be changed.

Distal ends of the air feeding pipes 62 to 64 are each connected to the pipe line 5 by being exposed into the pipe line 5. Multiple holes for feeding fine air bubbles into the pipe line 5 are formed at each of the distal ends of the air feeding pipes 62 to 64. Diameters of the holes vary from one air feeding pipe to another, and have predetermined values in a range of, for example, 0.01 µm to 1000 µm. Air bubbles generated from holes having diameters of 1 µm to 100 µm are called microbubbles, and have specific properties including a property of staying for a longer time period in liquid without bursting, than air bubbles having other diameters.

The switching unit 65 is provided at a place where the air generator 61 intersects with the air feeding pipes 62 to 64 and the switching unit 65 changes the air feeding pipe/pipes through which the air generated by the air generator 61 is fed. Sizes of the air bubbles generated by the air bubble generator 6 are thereby able to be changed. The switching unit 65 may select only one of the air feeding pipes 62 to 64 to send the air, but may select more than one of the air feeding pipes 62 to 64 and freely change the ratio between flow rates therethrough.

The circulation generator 7 includes a pump and a flowmeter. The circulation generator 7 is positioned downstream from the air bubble generator 6 along the direction in which the liquid flows. The circulation generator 7 outputs a flow rate or a flow velocity measured by the flowmeter, to the control device 9, and causes the liquid including air bubbles generated by the air bubble generator 6 to circulate at a predetermined flow rate or flow velocity under control of the control device 9. The circulation generator 7 may be provided downstream from the air bubble generator 6 as illustrated in FIG. 1, or may be provided upstream of the air bubble generator 6.

Figure 3:
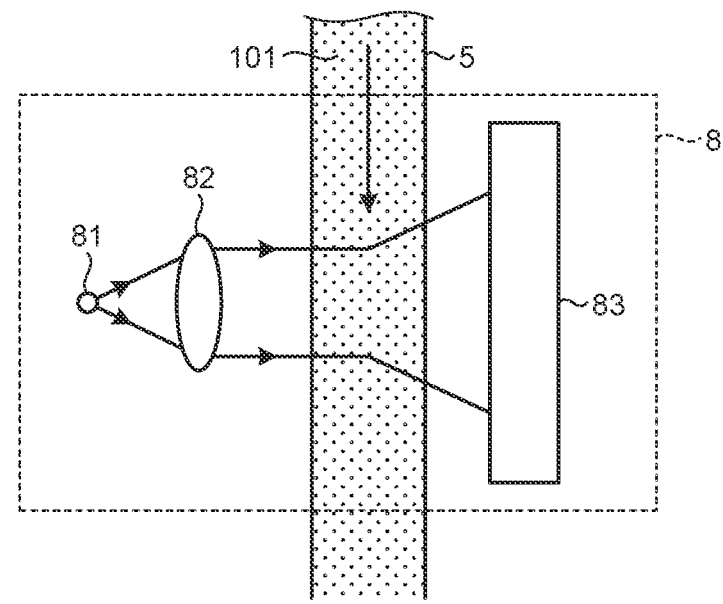
FIG. 3 is a diagram schematically illustrating a configuration of the air bubble generator.

The air bubble detecting device 8 detects sizes of air bubbles in the liquid collected from the balloon catheter 3. FIG. 3 is a diagram schematically illustrating a configuration of the air bubble detecting device 8. In FIG. 3, a downward arrow written in the pipe line 5 indicates the direction in which the liquid 101 flows. The air bubble detecting device 8 includes a light source 81 that generates light, an optical system 82 that forms the light generated by the light source 81 into parallel light and outputs the parallel light to the pipe line 5, and a detector 83 that receives the parallel light output by the optical system 82 and transmitted through the pipe line 5. The detector 83 detects, on the basis of information on the parallel light received, a state of diffusion in the liquid, calculates the size and concentration of the air bubbles, and outputs the size and concentration calculated, to the control device 9. A portion of the pipe line 5 is, of course, configured to be capable of transmitting the parallel light output by the optical system 82, the portion being where the air bubble detecting device 8 is provided. For the detector 83 to detect the state of diffusion in the liquid 101 and to detect the size and concentration of the air bubbles, light emitted to the pipe line 5 is ideally parallel light, but is not necessarily parallel light.

The air bubble detecting device 8 is provided downstream from and near the air bubble generator 6 along the direction in which the liquid flows. The air bubble detecting device 8 is preferably installed at a position where a distance between the air bubble generator 6 and the distal end portion 32 of the balloon catheter 3 equals a distance between the distal end portion 32 and the air bubble detecting device 8. As a result, estimation accuracy for the diameter and concentration of the air bubbles in the liquid 101 filling the distal end portion 32 is improved and the air bubble generator 6 is able to be caused to generate suitable air bubbles.

The control device 9 outputs a control signal to the air bubble generator 6 and the circulation generator 7, on the basis of: the diameter, concentration, and diameter distribution of the air bubbles detected by the air bubble detecting device 8; and a diameter, a concentration, and a diameter distribution of air bubbles that have been set beforehand. The control device 9 is a processor formed of one, or a combination of more than one, selected from a hardware group of: general-purpose processors, such as central processing units (CPUs); and dedicated integrated circuits that execute specific functions, such as field programmable gate arrays (FPGAs).

Figure 5:
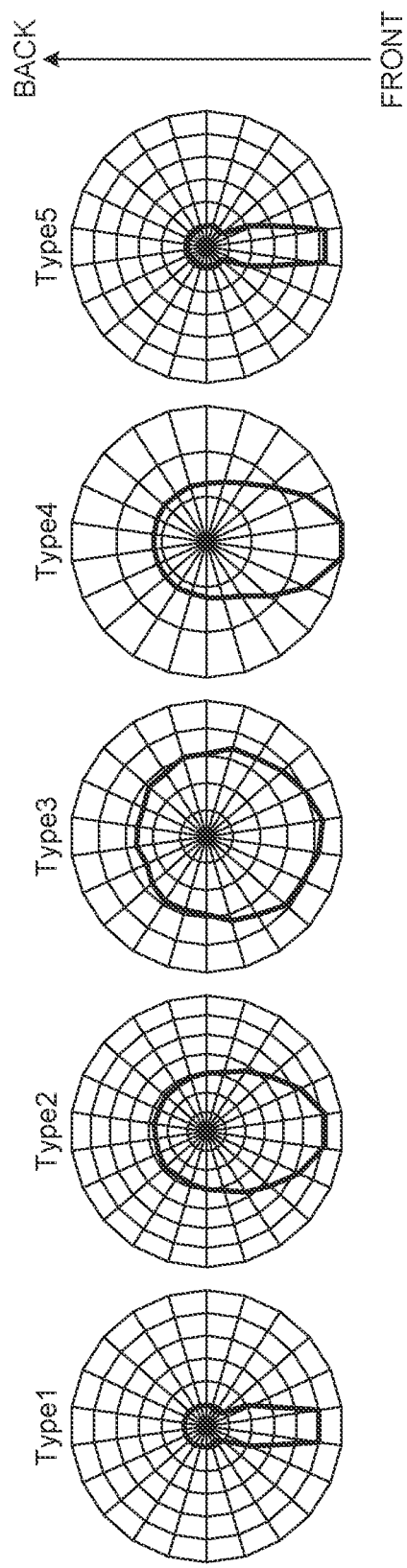
FIG. 5 is a diagram illustrating relations between the parameters and intensity distributions of light emitted by a light emitter.

When the light emitter 22 in the light treatment system 1 having the above configuration emits light, multiple scattering occurs in the distal end portion 32 of the balloon catheter 3 due to the air bubbles in the liquid. The intensity distribution caused by the multiple scattering varies according to conditions, such as the diameter and concentration of the air bubbles. This has been shown by the Mie scattering theory. FIG. 4 is a diagram illustrating an example of settings of parameters for treatment. In FIG. 4, there are five different combinations of diameters and concentrations (the numbers of air bubbles per unit volume) of air bubbles, and the other parameters are the same. FIG. 5 is a diagram illustrating relations between these parameters and irradiation intensity distributions of light emitted by the light emitter 22. In FIG. 5, a proximal end (the back) of the light emitter 22 is upward in the figure and a distal end (the front) of the light emitter 22 is downward in the figure.

As evident from FIG. 4 and FIG. 5, changing the diameter and concentration of the air bubbles enables the irradiation intensity distribution of light to be changed. For example, Type 3 has the most even irradiation intensity distribution of light, and Type 1 and Type 5 have irradiation intensity distributions of light that are localized forward the most. Both the diameter and the concentration of the air bubbles for Type 3 are the largest among the five examples. In contrast, one of the diameter and the concentration of the air bubbles for each of Type 1 and Type 5 is the largest and the other one thereof is the smallest, among the five examples.

Figure 6:
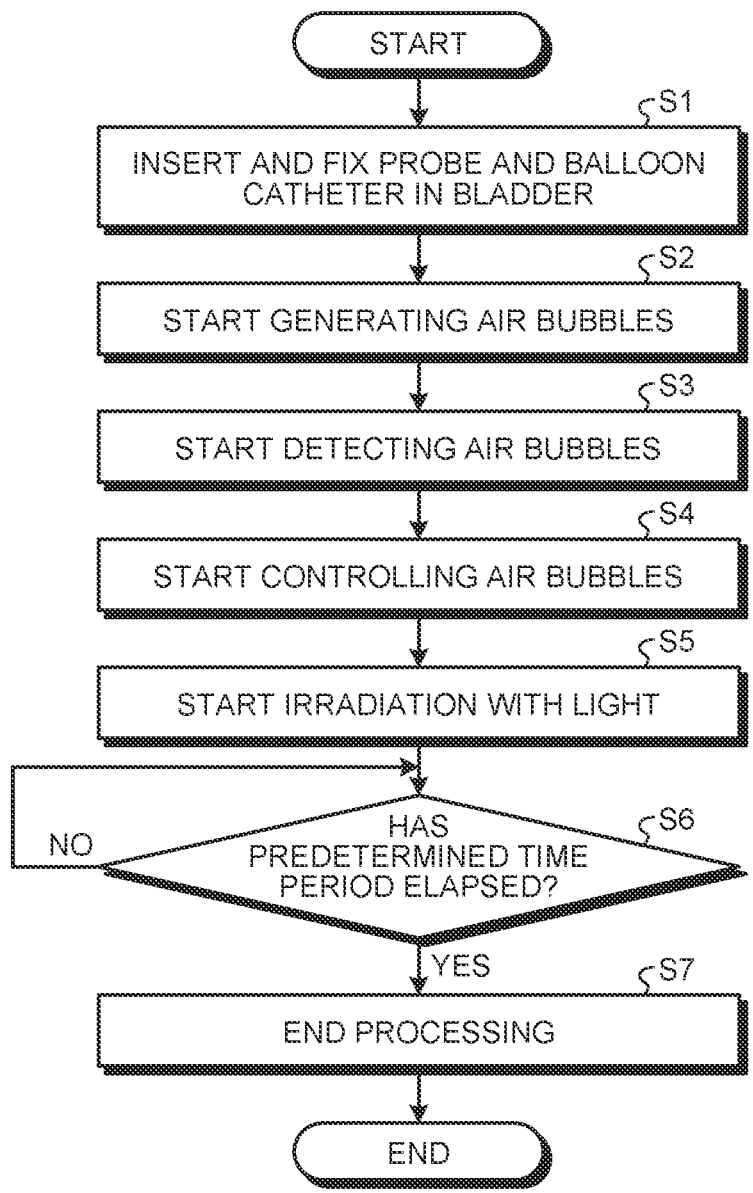
FIG. 6 is a flowchart illustrating an outline of a light treatment method using the light treatment system according to the embodiment.

FIG. 6 is a flowchart illustrating an outline of a light treatment method according to the embodiment. Details of the light treatment method will be described below by reference to FIG. 6.

Figure 7:
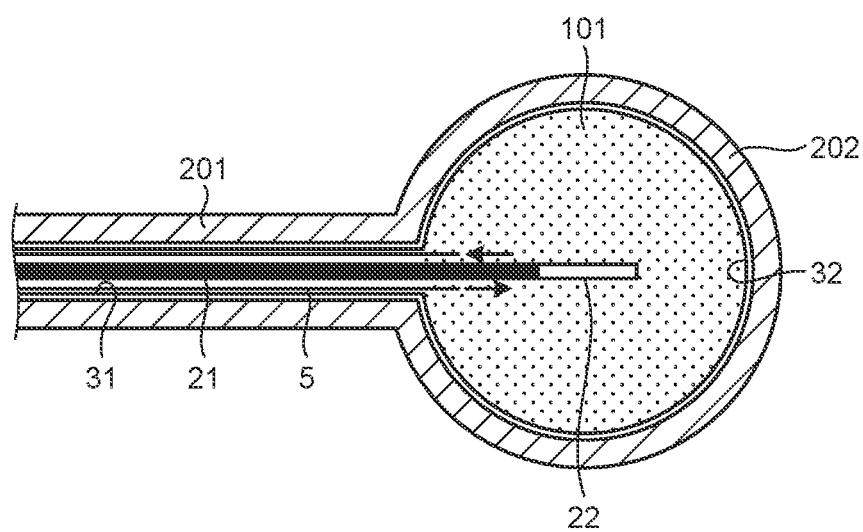
FIG. 7 is a diagram illustrating a state where a probe and a balloon catheter have been inserted from a urethra and the balloon catheter has been dilated and fixed inside the bladder.

First of all, the probe 2 and the balloon catheter 3 are inserted and fixed in the bladder of a patient (Step S1). Specifically, the balloon catheter 3 is inserted from the urethra and caused to reach the bladder first, and the probe 2 is thereafter inserted. Thereafter, by adjusting the flow rate and/or pressure of a liquid and supplying the liquid to the distal end portion 32 for dilation, the circulation generator 7 dilates the distal end portion 32 of the balloon catheter 3. FIG. 7 is a diagram schematically illustrating a state where the probe 2 and the balloon catheter 3 have been inserted from a urethra 201 into a bladder 202 and thereafter the balloon catheter 3 has been dilated and fixed by supply of the liquid 101. In the state illustrated in FIG. 7, the balloon catheter 3 and the bladder 202 are in contact with each other via a small amount of urine. By controlling the size of the balloon catheter 3, a surface of the bladder 202 is able to be dilated without being wrinkled and efficient irradiation with light output by the probe 2 is enabled. If the probe 2 and the balloon catheter 3 are integrated with each other, the integrated probe 2 and balloon catheter 3 may be inserted from the urethra 201 and caused to reach the bladder 202 and thereafter the balloon catheter 3 may be dilated by supply of the liquid 101 to the distal end portion 32.

After Step S1, the air bubble generator 6 starts generating air bubbles under control of the control device 9 (Step S2). The control device 9 controls operation of the air bubble generator 6 on the basis of a diameter and a concentration of air bubbles that have been set beforehand.

Subsequently, the air bubble detecting device 8 starts detecting air bubbles (Step S3). Specifically, the air bubble detecting device 8 measures the diameter and the concentration of air bubbles in a liquid including air bubbles that has passed through the balloon catheter 3 and outputs the measured diameter and concentration to the control device 9.

The control device 9 determines an optimum diameter and an optimum concentration of air bubbles on the basis of a result of the detection by the air bubble detecting device 8 and the set values, and starts processing of outputting a control signal to the air bubble generator 6.

Thereafter, the power of the light source device 4 is turned on to start emission of light into the bladder (Step S5).

If a predetermined time period has elapsed from start of irradiation with light at Step S5 (Step S6: Yes), processing to end the treatment by the light treatment system 1 is performed (Step S7). Specifically, the power of the light source device 4 is turned off to end the emission of light into the bladder, operation of the air bubble generator 6 is thereafter ended, and the circulation generator 7 reduces the pressure in the circulation to contract the distal end portion 32. Subsequently, in the order of the probe 2 and the balloon catheter 3, the probe 2 and the balloon catheter 3 are removed from the bladder to outside of the body.

If, at Step S6, the predetermined time period has not elapsed (Step S6: No), Step S6 is repeated.

According to the embodiment described above, because a liquid including air bubbles corresponding to light scattering particles is supplied to a distal end portion of a balloon catheter and properties of the air bubbles are made changeable, modes of irradiation with light for treatment are able to be changed readily.

Furthermore, according to the embodiment, because modes of circulation are made changeable for circulation of a liquid including air bubbles via a balloon catheter, modes of irradiation with light for treatment are able to be changed even more finely.

OTHER EMBODIMENTS

One embodiment of the disclosure has been described above, but the disclosure should not be limited only to the embodiment described above.

Figure 8:
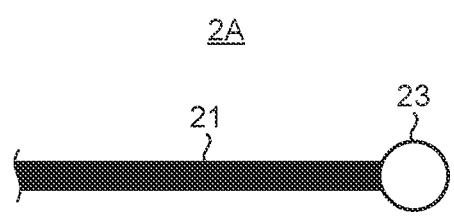
FIG. 8 is a diagram illustrating a first modified example of a structure of a distal end of the probe.
Figure 9:
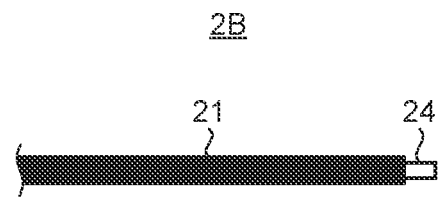
FIG. 9 is a diagram illustrating a second modified example of the structure of the distal end of the probe.

For example, the shape of a light emitter is not limited to the cylindrical shape described above. Specifically, the light emitter may be a spherical light emitter 23 like in a probe 2A illustrated in FIG. 8, or a front-emitting light emitter 24 without a diffusing function like in a probe 2B illustrated in FIG. 9.

Furthermore, although the case where the inside of a bladder is treated has been described above as an example, the above described light treatment system and light treatment method are applicable to treatment of inside of body cavities other than bladders.

Accordingly, the disclosure may include various embodiments not described herein.

The disclosure facilitates change of modes of irradiation with light for treatment.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light treatment system, comprising:
   a probe configured to be inserted into a body cavity, the probe including an optical fiber configured to propagate light, and a light emitter that is provided at a distal end of the optical fiber, the emitter being configured to emit the light;
   a balloon catheter into which the probe is inserted, the balloon catheter including a distal end portion that is to be inserted into the body cavity and that is to be dilated by being supplied with a liquid including air bubbles; and
   an air bubble generator configured to generate the air bubbles to be included in the liquid, the air bubble generator further being configured to change a property of the air bubbles,
   wherein the air bubble generator includes an air generator configured to generate air with variable pressure, and the air bubble generator is configured to vary the pressure of the air to be generated from the air generator to thereby change a concentration of the air bubbles in the liquid.

2. The light treatment system according to claim 1, further comprising:
at least one processor; and
a circulation generator configured to circulate, through the balloon catheter, the liquid including the air bubbles generated by the air bubble generator, wherein the circulation generator comprising:
a pump, and
a flowmeter configured to measure at least one of a flow rate and a flow velocity of the liquid in the balloon catheter,
wherein the circulation generator is configured to output the at least one of the flow rate and the flow velocity measured by the flowmeter, to the at least one processor, and
the at least one processor is configured to control the pump based on the at least one of the flow rate and the flow velocity output to the at least one processor to thereby change a mode of a circulation of the liquid.

3. A light treatment method, comprising:
inserting a balloon catheter and a probe into a body cavity, the balloon catheter including a distal end portion that is dilatable, the probe being configured to propagate light for treatment and emit the light propagated, the probe being configured to be inserted into the balloon catheter;
fixing the distal end portion in the body cavity by circulating a liquid through the distal end portion to dilate the distal end portion;
starting a process of generating air bubbles and causing the air bubbles to be included in the liquid, the process comprising:
measuring diameters and a concentration of air bubbles in the liquid that have passed through the balloon catheter; and
by at least one processor, based on a result of the measurement of the diameters and the concentration of the air bubbles and on diameters and a concentration that have been preset for the air bubbles, performing feedback control of at least one of a flow rate and a pressure at which the liquid is to be circulated and of diameters and a concentration of the air bubbles to be generated; and
irradiating inside of the body cavity with the light from the probe.

4. A light treatment system, comprising:
a probe configured to be inserted into a body cavity, the probe including an optical fiber configured to propagate light, and a light emitter that is provided at a distal end of the optical fiber, the emitter being configured to emit the light;
a balloon catheter into which the probe is inserted, the balloon catheter including a distal end portion that is to be inserted into the body cavity and that is to be dilated by being supplied with a liquid including air bubbles; and
an air bubble generator configured to generate the air bubbles to be included in the liquid, the air bubble generator being further configured to change a property of the air bubbles,
wherein the air bubble generator includes a plurality of air feeding pipes, each of the plurality of air feeding pipes having a distal end provided with multiple holes through which air passes to generate the air bubbles,
the multiple holes of each of the plurality of air feeding pipes have diameters varying from one air feeding pipe to another, and
the air bubble generator is configured to selectively feed the air into the plurality of air feeding pipes to change diameters of the air bubbles.

5. The light treatment system according to claim 4, wherein the diameters of the multiple holes have predetermined values in a range of 0.01 μm to 1000 μm.

6. The light treatment system according to claim 5, wherein the diameters of the multiple holes have predetermined values in a range of 1 μm to 100 μm.

7. The light treatment system according to claim 1, further comprising:
at least one processor; and
a circulation generator configured to circulate, through the balloon catheter, the liquid including the air bubbles generated by the air bubble generator, wherein
the circulation generator comprises:
a pump, and
a flowmeter configured to measure at least one of a flow rate and a flow velocity of the liquid in the balloon catheter,
the circulation generator is configured to output the at least one of the flow rate and the flow velocity measured by the flowmeter, to the at least one processor, and
the at least one processor is configured to perform feedback control of the pump based on the at least one of the flow rate and the flow velocity output to the at least one processor to thereby change a mode of a circulation of the liquid.

8. The light treatment system according to claim 7, further comprising an air bubble detecting device configured to detect diameters of the air bubbles in the liquid collected from the balloon catheter.

9. The light treatment system according to claim 8, wherein
the air bubble detecting device is configured to output the detected diameters of the air bubbles to the at least one processor, and
the at least one processor is configured to perform feedback control of the air bubble generator based on the detected diameters of the air bubbles to thereby change the diameters of the air bubbles.

10. The light treatment system according to claim 8, wherein the air bubble detecting device comprises:
a light source configured to generate light,
an optical system configured to output the light generated by the light source, and
a detector configured to receive the light that is output from the optical system and is transmitted through the liquid including the air bubbles passing through the balloon catheter.

11. The light treatment system according to claim 10, wherein the light output from the optical system is parallel light.

12. The light treatment system according to claim 2, further comprising an air bubble detecting device configured to detect the concentration of the air bubbles in the liquid collected from the balloon catheter.

13. The light treatment system according to claim 12, wherein the air bubble detecting device is configured to output the detected concentration of the air bubbles to the at least one processor, and the at least one processor is configured to perform feedback control of the air bubble generator based on the detected concentration of the air bubbles to thereby change the concentration of the air bubbles.

14. The light treatment system according to claim 12, wherein the air bubble detecting device comprises:

a light source configured to generate light, an optical system configured to output the light generated by the light source, and a detector configured to receive the light that is output from the optical system and is transmitted through the liquid including the air bubbles passing through the balloon catheter.

15. The light treatment system according to claim 14, wherein the light output from the optical system is parallel light.

* * * * *